(12) United States Patent
Welch et al.

(10) Patent No.: US 9,408,573 B2
(45) Date of Patent: Aug. 9, 2016

(54) PATIENT INTERFACE FOR REUSABLE OPTICAL SENSOR

(75) Inventors: Randall Welch, Mission Viejo, CA (US); Gwenn Ellerby, Natick, MA (US); Peter Scott, Auburn, MA (US); Babs Soller, Cambridge, MA (US); Edward Rowan, Concord, MA (US)

(73) Assignee: Sotera Wireless, Inc., San Diego, CA (US)

( * ) Notice: Subject to any disclaimer, the term of this patent is extended or adjusted under 35 U.S.C. 154(b) by 883 days.

(21) Appl. No.: 13/570,939

(22) Filed: Aug. 9, 2012

(65) Prior Publication Data

US 2015/0297137 A1  Oct. 22, 2015

Related U.S. Application Data

(60) Provisional application No. 61/522,494, filed on Aug. 11, 2011.

(51) Int. Cl.
*A61B 5/00* (2006.01)
*A61B 5/1455* (2006.01)
*A61B 5/145* (2006.01)

(52) U.S. Cl.
CPC ........... *A61B 5/6833* (2013.01); *A61B 5/14535* (2013.01); *A61B 5/14539* (2013.01); *A61B 5/14551* (2013.01); *A61B 5/14552* (2013.01); *A61B 5/6823* (2013.01); *A61B 5/6824* (2013.01); *A61B 5/6828* (2013.01); *A61B 5/6831* (2013.01); *A61B 2560/0412* (2013.01); *A61B 2560/0443* (2013.01);

(Continued)

(58) Field of Classification Search
CPC .......................................................... A61B 5/00
USPC ........................................................ 235/492
See application file for complete search history.

(56) References Cited

U.S. PATENT DOCUMENTS 6,920,345 B2     7/2005   Al-Ali et al.
7,460,897 B1 *  12/2008   Flessland et al. ............. 600/344
8,505,821 B2 *   8/2013   Medina et al. ................ 235/454

(Continued)

FOREIGN PATENT DOCUMENTS

EP          0756847 A1       2/1997
WO       WO 2013/023071      2/2013

OTHER PUBLICATIONS

International Search Report and Written Opinion mailed Nov. 27, 2012 in International Application No. PCT/US2012/050167.

(Continued)

*Primary Examiner* — Toan Ly
(74) *Attorney, Agent, or Firm* — Sean D. Detweiler, Esq.; Morse, Barnes-Brown & Pendleton, P.C.

(57) ABSTRACT

A patient interface for a reusable optical sensor, the patient interface including a compliant element defining a pocket having a lower wall defining an opening therethrough, the pocket being configured to removably receive the reusable optical sensor. The compliant element includes a first wing and a second wing configured for conformal placement on a patient's body. A condition of a patient may be monitored by inserting an optical sensor into a patient interface, applying the patient interface to the patient, obtaining a measurement with the optical sensor related to the condition of the patient, removing the patient interface from the patient, and removing the sensor from the patient interface.

27 Claims, 17 Drawing Sheets

(52) U.S. Cl.
CPC .... *A61B 2562/146* (2013.01); *A61B 2562/164* (2013.01); *A61B 2562/18* (2013.01); *A61B 2562/247* (2013.01)

(56) References Cited

U.S. PATENT DOCUMENTS

2004/0147822 A1    7/2004    Al-Ali et al.
2006/0074283 A1*   4/2006    Henderson et al. ........... 600/315
2009/0024013 A1    1/2009    Soller et al.
2010/0130875 A1*   5/2010    Banet et al. ................... 600/490
2011/0205535 A1    8/2011    Soller et al.
2012/0123232 A1*   5/2012    Najarian et al. .............. 600/345

OTHER PUBLICATIONS

International Preliminary Report on Patentability mailed Feb. 11, 2014 in International Application No. PCT/US2012/050167.

* cited by examiner

SECTION B-B

PATIENT INTERFACE FOR REUSABLE OPTICAL SENSOR

CROSS-REFERENCE TO RELATED APPLICATION

This application claims priority to U.S. Provisional Application Ser. No. 61/522,494, filed on Aug. 11, 2011, the entire disclosure of which is hereby incorporated by reference.

FEDERALLY SPONSORED RESEARCH

The work related to this subject matter was performed with government support under Grant Nos. W81XWH-08-C-0114 and W81XWH-11-C-0001 awarded by the US Army Medical Research and Materiel Command. The government may have certain rights to the invention.

BACKGROUND

Referring to FIGS. 1a-1c, sensor assemblies 100 with foam pads and embedded sensors are used to monitor patients. See, e.g., the InSpectra™ device by Hutchinson Technology shown in FIGS. 1a-1c, or the EQUANOX™ from Nonin Medical Inc. In such devices, a sensor shield is permanently attached to the sensor. The sensor assembly may include a foam piece with an adhesive and a liner; the foam piece may have openings for LEDs and detectors. After use, the entire sensor assembly, including the sensor, is thrown away. Such devices therefore utilize relatively unsophisticated sensor technology, limiting the usefulness and accuracy of the patient monitoring system.

SUMMARY

In one aspect, certain embodiments of the invention feature a patient interface for a reusable optical sensor. The patient interface includes a compliant element defining a pocket having an upper wall and a lower wall and configured to removably receive the reusable optical sensor, the lower wall of the pocket defining an opening therethrough, the compliant element including a first wing and a second wing configured for conformal placement on a patient's body. The compliant element includes a contact surface, and the opening extends from inside the pocket through the lower wall to the contact surface.

One or more of the following features may be included. The compliant element may include or consist essentially of open celled foam, closed cell foam, natural rubber, synthetic rubber, thermoplastic elastomer, and/or fabric. The compliant element may include a moisture impervious surface. At least one of the wings may define an opening therethrough. The compliant element may be sized and configured to conform to a portion of a patient's body, such as a deltoid, an upper arm, a calf, a thigh, a forearm, a lower back, or an upper back.

The compliant element may include a nose disposed at an end of the compliant element remote from an open end of the pocket. The nose may be angled toward the contact surface and/or may have a tapered profile to provide shielding of the optical sensor from ambient light.

The patient interface may include at least one upper wall protrusion to bias an optical sensor disposed in the pocket toward the lower wall of the pocket. At least one lower wall protrusion may be disposed proximate an entrance of the pocket to facilitate retention of the optical sensor in the pocket.

The patient interface may include an adhesive layer disposed on at least a portion of the contact surface of the compliant element. The adhesive layer may include a transfer adhesive. A removable liner may be disposed proximate the adhesive layer. The removable liner may be optically transparent.

The patient interface may further include n optically clear window aligned with the lower wall opening. The optically clear window may include an adhesive layer along at least a portion thereof. The optically clear window may include an optical tape.

The pocket may be sized to receive the sensor with a sliding interference fit.

A rigid component may be disposed along at least a portion of an outer surface of the compliant element or embedded within the element proximate the pocket. The rigid component may include or consist essentially of a plastic, a metal, and/or a composite material to protect the optical sensor.

The compliant element may include or consist essentially of fabric. The patient interface may further include a first strap attached to one of the two wings, the first strap being configured for encircling a portion of a patient's body. A fastener may be attached to an other of the two wings, adapted to receive and secure the first strap. A second strap may be attached to the other of the two wings and the fastener may be attached the second strap. The first strap may include a hook-and-loop fastener. The lower wall of the pocket may include a non-slip material.

In another aspect, embodiments of the invention include a method of monitoring a condition of a patient. The method includes inserting an optical sensor into a patient interface, and applying the patient interface to the patient. A measurement is obtained with the optical sensor related to the condition of the patient. The patient interface is removed from the patient, and the sensor is removed from the patient interface.

The patient interface may be disposed of, and the optical sensor reused in a new patient interface to obtain an additional measurement.

DETAILED DESCRIPTION

Figure 1A:
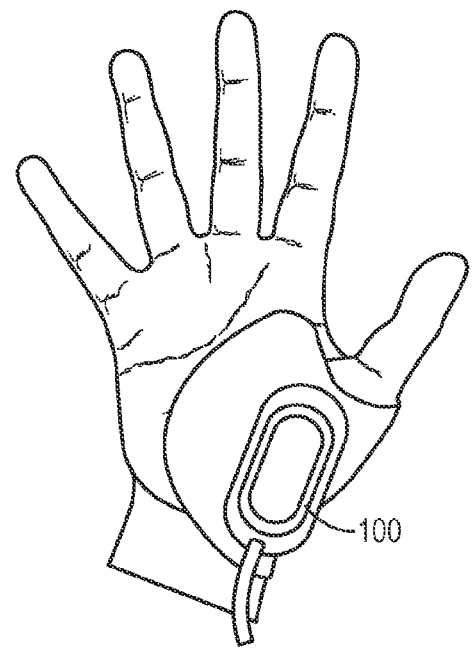
FIGS. 1a-1c are schematic drawings illustrating a prior art sensor assembly.
Figure 1B:
Figure 1C:
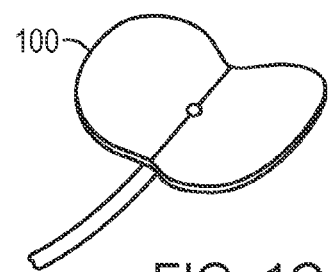

In an embodiment, a spectroscopic-based optical sensor measures multiple parameters (such as, for example $SmO_2$, pH and/or Hct) that are valuable in the care of trauma and other critically ill patients. See, e.g., the type disclosed in U.S. patent application Ser. No. 13/057,617, the disclosure of which is incorporated herein in its entirety. The sensor may be applied on the battlefield, at the scene of an accident, in an emergency transport vehicle or in the operating room, the ICU, emergency room or other parts of a hospital. It typically remains attached to the patient for several days.

The sensor may also be used during sports and exercise. See U.S. patent application Ser. No. 12/172,942, the disclosure of which is incorporated herein in its entirety, or at home for monitoring patients with chronic diseases. In this embodiment, the sensor is preferably held firmly against the skin by, e.g., a stand-alone pocket or a pocket in an article of clothing, but is removable so that the pocket or garment may be washed.

Embodiments of the patient interface for a spectroscopic-based optical sensor, referred to herein also as the ray due to its peripheral shape and concave contouring, may provide one or more of the following advantages:

1. A clean patient interface for each new patient of this reusable sensor.
2. An opaque area around the spectroscopic detector to prevent ambient light from reaching the detector through the skin, while keeping the inflexible sensor case as small as possible.
3. An optically clear window for NIR spectral analysis.
4. A method for ensuring complete physical contact between the sensor optics, window material and the skin.
5. A single size that fits a number of anatomical areas and sizes.
6. Capability to have the sensor removed and re-inserted without removing the ray from the patient (for transport to MRI).
7. Biocompatible (per FDA standards) and may be designed to be manufactured in high volume.
8. Ventilation to the skin under the pad.

Critically ill patients are typically carefully protected from the risk of infection. One approach to help meet this goal is to make the entire sensor and its attachment mechanism disposable. Some sensors are presently too expensive to be disposed of after every patient use. Reusable medical devices can be cleaned between patient use; however, improper cleaning can increase the risk of patient infection, which may be a serious problem for critically ill patients. Embodiments of this invention, such as the "ray," provide a sheath to cover the entire sensor, so that only a simple cleaning and disinfecting process of the surface of the sensor is required. The ray is an inexpensive part that simplifies the reuse of sensors, and, thereby, may reduce the overall cost of the use of sensor assemblies, while also reducing the risk of infection.

Double-sided adhesive may be used on the patient contact surface of the sensor. A drawback of this approach is that the sensor case may need to be large to ensure that the skin adjacent to the sensitive spectroscopic sensor does not transmit ambient light. Also, a large, rigid case does not fit well onto rounded muscles, which are typically the target placement areas for the sensor. The ray is flexible, and conforms to a variety of placement locations, while allowing for a narrow sensor case and good contact for the optical elements, while providing desirable ambient light isolation.

Prior approaches include (1) taping the sensor to the skin and covering it with a dark cloth; (2) using an optically clear double-sided adhesive on a large rigid case; and (3) throwing the entire sensor away. The ray is designed to contain the appropriate equivalent of a double-sided adhesive, i.e., a single-sided adhesive for patient contact, but also allows the sensor to slip inside. After a patient measurement is made, the sensor may be removed and may require minimal, if any, cleaning before it is ready to be used on a new patient. This approach allows rapid placement and use of the sensor, which is important in providing treatment to casualties and other critically ill patients who require rapid medical attention.

The ray is designed with several advantageous features that allow it to conform to a large range of anatomical surfaces (muscles) and to ensure that the sensor provides the appropriate optical contact and transparency for accurate measurement.

Referring to FIGS. 2a-11c, in various embodiments, a patient interface 200 for a reusable optical sensor may include a compliant element 210. The compliant element 210 may be made from a flexible and resilient material, such as open celled foam, closed cell foam, natural rubber, synthetic rubber, and/or thermoplastic elastomer or other suitable material adapted to meet the objectives set forth herein. The compliant element may include a moisture impervious or resistant surface or skin. In some embodiments, the surface or skin may be an integral portion of the compliant element, e.g., a self-skinning foam. The surface or skin may, in other embodiments, be a coating. The moisture impervious surface enhances the appearance of the patient interface, and helps to repel water or sweat. The compliant element may be relatively soft, e.g., having a Shore A durometer in a range of 8 to 15, typically about 10. In alternative embodiments, the compliant element 210 may be formed from fabric; exemplary fabric embodiments are discussed below with reference to FIGS. 12-17.

Figure 2A:
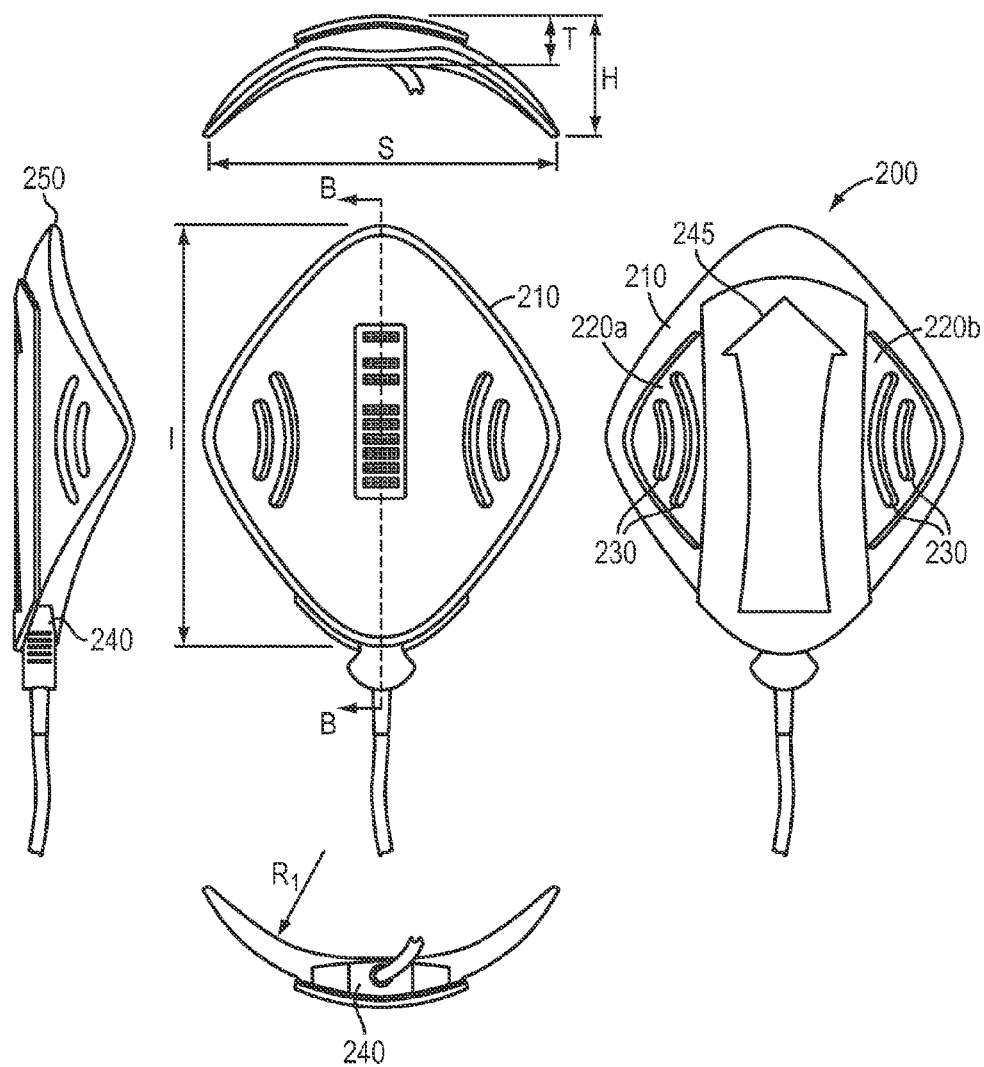
FIGS. 2a-2b includes schematic solid model, exploded, and cross-sectional views of a patient interface, in accordance with an embodiment of the invention.
Figure 2B:
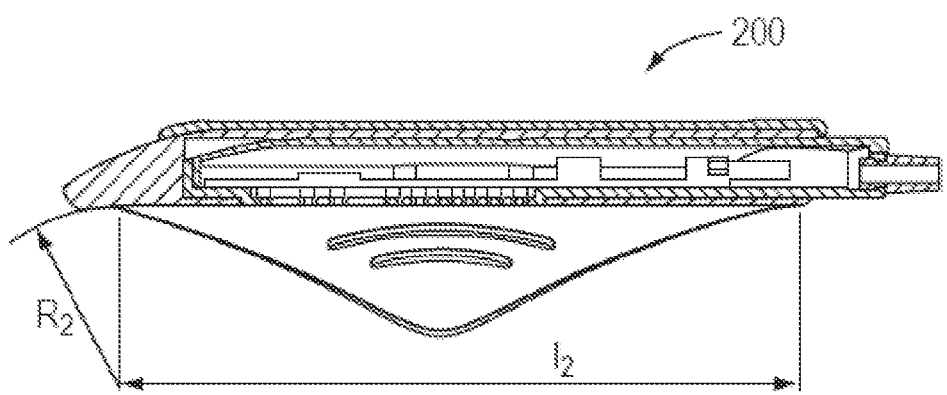

Referring to FIGS. 2a-2b, the compliant element may be symmetrical along a longitudinal centerline and may have a first wing 220a and a second wing 220b configured for conformal placement on a patient's body. At least one of the wings may define openings 230 therethrough. These openings help provide ventilation to keep skin underneath the compliant member from becoming too hot or sweaty.

The compliant member, including the wings, may be molded to define a curved shape, sized and configured to conform to a portion of a patient's body, e.g., to a deltoid, an upper arm, a calf, or a thigh, forearm, upper and lower back. The compliant member has a convex outer surface and a concave contact surface. The compliant member may be sufficiently long and sufficiently wide to fit snugly on the patient's body portion and effectively keep ambient light from reaching the spectroscopic detector. In an embodiment, the compliant member has a length 1 of about 10 mm to about 500 mm, preferably about 150 mm (5.9") and a span s of about 10 mm to about 500 mm, preferably about 130 mm (5.1"). A length $l_2$ of the ray, excluding a radius of the nose may be about 10 mm to about 500 mm, preferably about 133 mm (5.2"). A length of the wings may be approximately 115 mm (4.5"). When laid flat, a span s of the wings may be selected from a range of 25 mm (1") to about 1500 mm (60"), preferably about 150 mm (5.9"). A radius of curvature $R_1$ of the curved shape may be selected to conform to the patient's body portion, e.g., ranging from about 250 mm (9.8") to about 650 mm (26"). For example, the radius of curvature $R_1$ may be about 10 mm to about 250 mm, preferably about 76 mm (3") in some embodiments. A height H of the compliant member is a result of (i) the selected appropriate radius of curvature $R_1$ that takes into account a size and shape of a body part, and (ii) the wingspan that is needed to block out light. A suitable height H may range from about 5 mm to about 75 mm, preferably about 43 mm (1.7") in some embodiments. If the compliant member were to be flattened, it would generally define a rhombus shape.

At least one of the wings 220a, 220b may have a thinned portion, to help mold the compliant member to rounded muscle.

As discussed further with respect to FIG. 4, compliant member 210 may include a pocket 240 for receiving an optical sensor.

The compliant member 210 is preferably dark-colored or black, thereby helping prevent ambient light from reaching an optical sensor disposed in the pocket.

The patient interface may include a rigid component 245 disposed on an outer surface of the compliant element or embedded within the element above the pocket 240. This rigid component facilitates sliding an optical sensor into the pocket and may provide additional protection to the sensor. The rigid component may be formed from a rigid material, such as a plastic, a metal, and/or a composite material. A total thickness T of the compliant member and the rigid component may be from 7 mm to about 35 mm, preferably about 15 mm (0.6"). The rigid component is preferably thick enough to be molded with standard molding processes, but not so thick as to add substantial weight and height to the ray.

Figure 3:
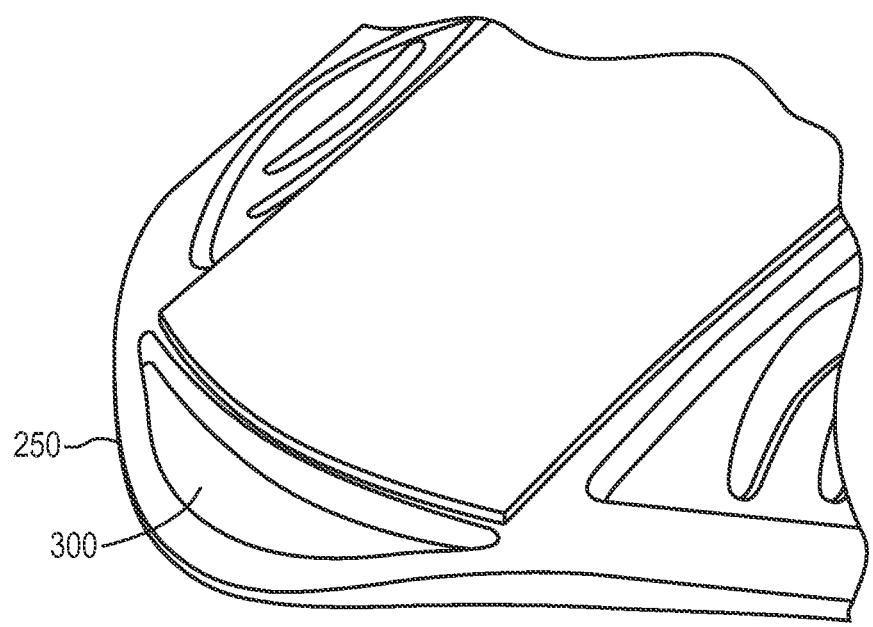
FIG. 3 is a schematic view of a patient interface with a thinned nose with a pocket, in accordance with an embodiment of the invention.

Referring to FIGS. 2a-3, the compliant element may include a nose 250 disposed at an end of the compliant element remote from an open end of the pocket. The nose may be angled toward the contact surface. This downward angling of the nose helps ensure that the tip does not lift up during use, thereby potentially exposing a detector in the sensor to light. The nose may have a radius of curvature $R_2$ of, e.g., about 25 mm to about 50 mm, preferably 38.1 mm (1.5"). The nose may have a tapered profile, i.e., it may be thinned to improve adherence of the compliant element to rounder muscles, e.g., in the shoulder and the calf. The thinned nose may include a pocket 300, with a surface tapered to match proximate wings to facilitate conformance to, e.g., a top of a shoulder.

Figure 4A:
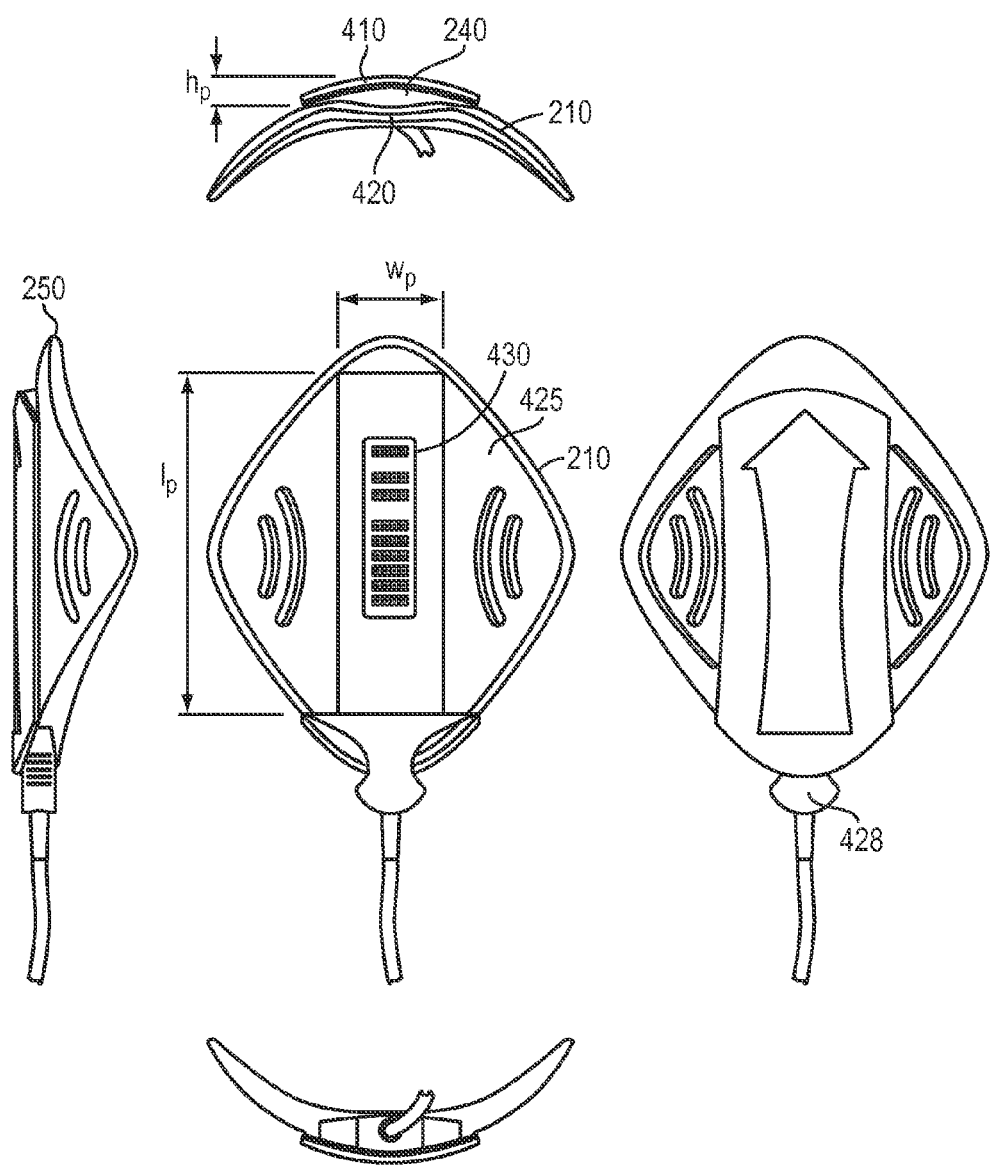
FIGS. 4a-4b include schematic plan, side, bottom, end, and cross-sectional views of a patient interface, in accordance with an embodiment of the invention.
Figure 4B:
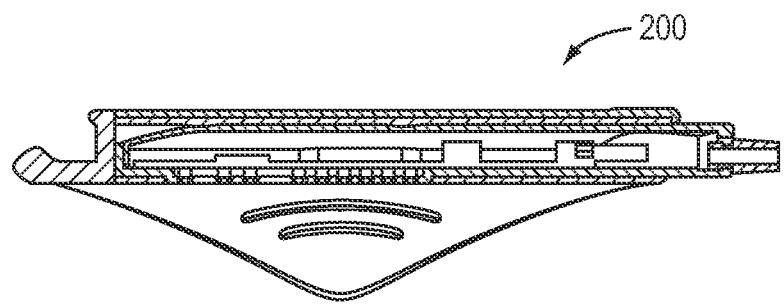

Referring to FIGS. 4a-4b, the compliant element 210 of a patient interface 200 may define a pocket 240 having an upper wall 410 and a lower wall 420. The lower wall 420 may form a portion of a contact surface 425 of the compliant element; in use, the contact surface may be the side of the compliant element that is in closest proximity to the patient's skin. The pocket may be sized and configured to removably receive a reusable optical sensor 428, such as the CareGuide™ sensor available from Reflectance Medical Inc. In some embodiments, the pocket may be sized to receive the sensor with a sliding interference fit. For example, the pocket may have a length $l_p$ of about 90 mm (3.5") to about 150 mm (5.9"), preferably about 120 mm (4.7"), width $w_p$ of about 35 mm (1.4") to about 55 mm (2.2"), preferably about 47 mm (1.8"), and a height $h_p$ of about 8 mm (0.31") to about 25 mm (0.98"), preferably about 13.4 mm (0.53").

The lower wall of the pocket may define an opening 430 therethrough, with the opening extending from inside the pocket through the lower wall to the contact surface. This opening may be positioned to align with the detectors and transmitters of a reusable optical sensor disposed in the pocket, e.g., with the detectors and transmitters of the optical sensor.

The pocket and compliant element may be sized so that an end of a fully inserted optical sensor extends beyond the patient interface, thereby facilitating the removal of the optical sensor from the pocket.

Figure 5:
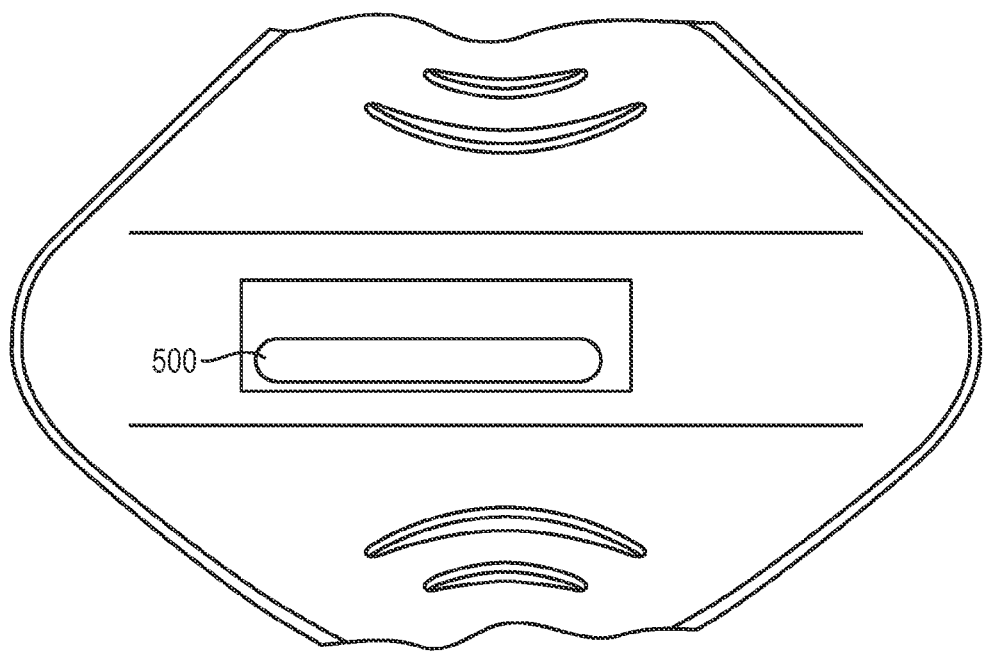
FIG. 5 is a schematic view of a protrusion in the form of an oblong feature, in accordance with an embodiment of the invention.

Referring to FIG. 5, at least one upper wall protrusion 500 may be disposed on the upper wall of the pocket to bias an optical sensor disposed in the pocket toward the lower wall of the pocket. The upper wall protrusion may be one or more domes, or it may be an oblong or other feature. The upper wall protrusion helps provide better contact between the sensor optics and the optically clear window (described below).

Figure 6:
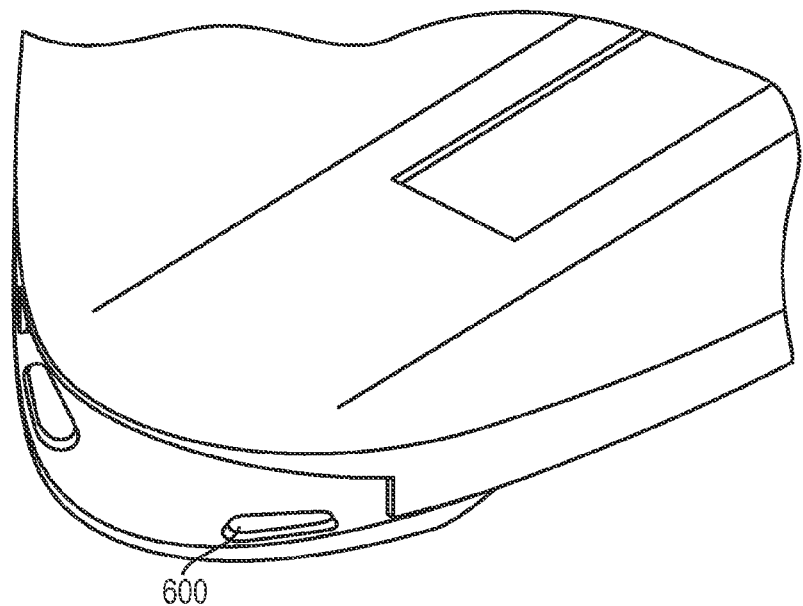
FIG. 6 is a schematic view of protrusions added to a pocket of a patient interface, in accordance with an embodiment of the invention.

Referring to FIG. 6, at least one lower wall protrusion 600 may be disposed proximate an entrance of the pocket, thereby helping facilitating retention of the optical sensor in the pocket when, for example, the sensor is attached to a vertical limb.

The compliant element may be formed by, e.g., injection molding.

Figure 7A:
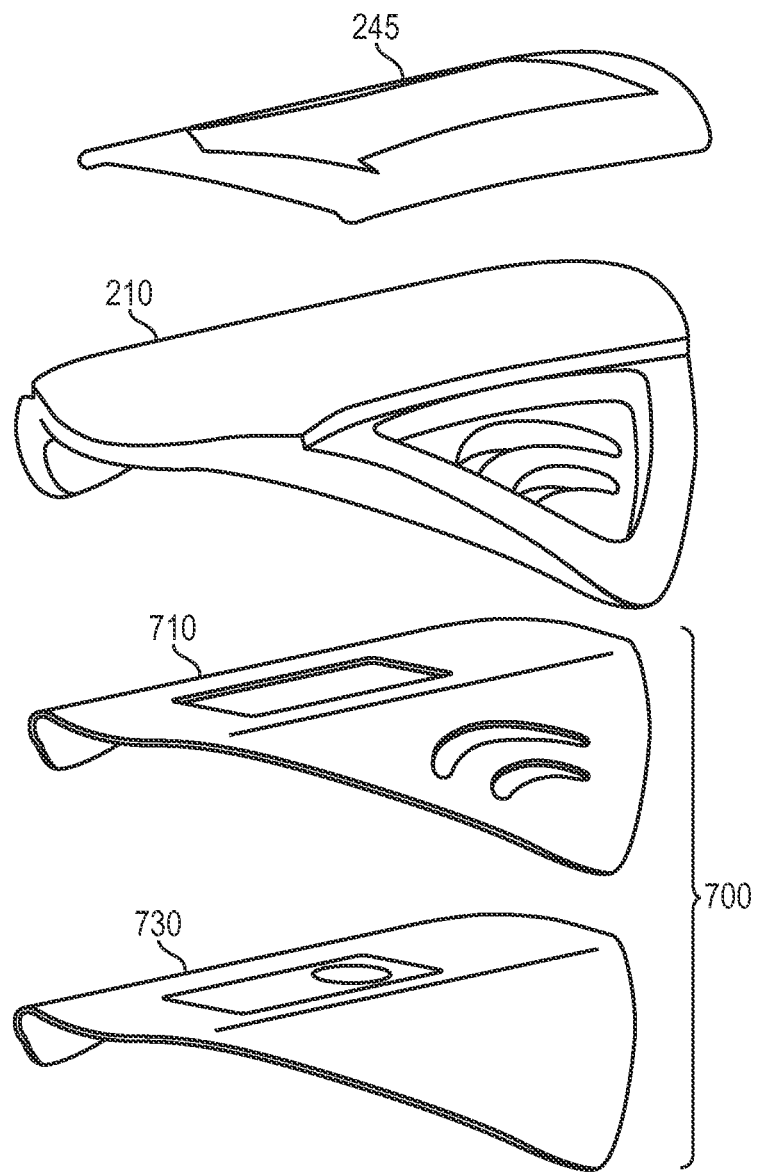
FIGS. 7a-7b are schematic views of an adhesive stack including a transfer adhesive, an optical tape, and a removable liner.
Figure 7B:
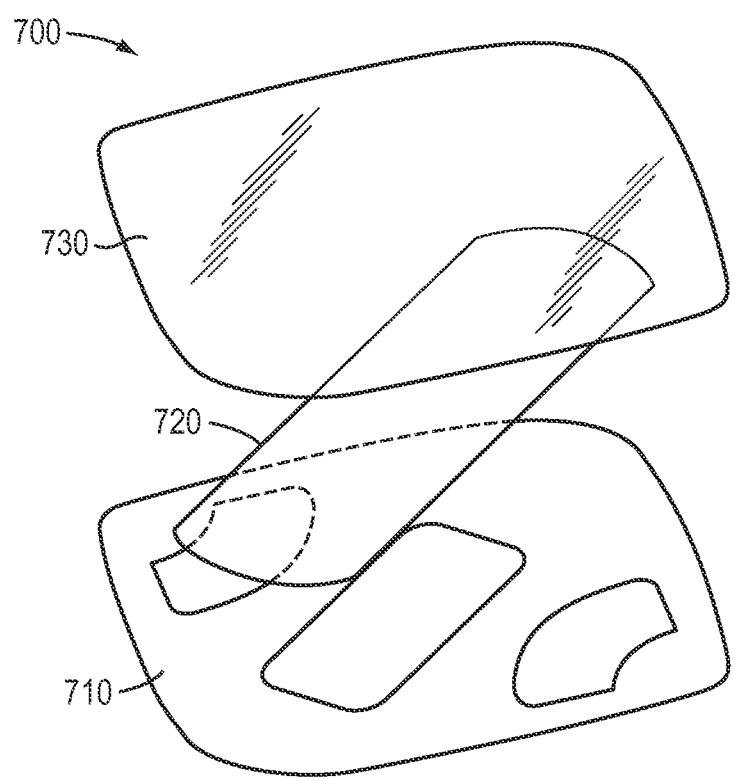

Referring to FIGS. 7a and 7b, an adhesive layer 700 with biocompatible components may be disposed on at least a portion of the contact surface of the compliant element. The adhesive layer may include a transfer adhesive 710, such as the 2120U transfer adhesive available from Avery Dennison. The transfer adhesive is preferably sufficiently strong to keep the patient interface securely in place during sensor measurements, while also allowing removal from the patient's body without damaging the skin. The transfer adhesive is preferably very thin, and may be used to maintain the flexibility of the wings, such that the compliant element may be conformed to rounded muscles of varying size, shape, and contour.

An optically clear window 720 may be aligned with the lower wall opening. The optically clear window may include an adhesive surface along at least a portion thereof. The optically clear window may include, for example, an optical tape such as 9793R diagnostic tape available from 3M. The optical tape preferably transmits light through a thickness of the tape, but does not transmit light longitudinally along a length of the tape. Longitudinal light transmission may interfere with sensor measurements, e.g., light from the sensor LEDs may be transmitted directly to the detector. The inside surface of the optically clear window may be free of adhesive, to not interfere with the movement of the optical sensor into and from the pocket. In use, the optical sensor is held directly against optical tape, such that there is substantially no air gap between the optical sensor and the optically clear window.

The adhesive element may include a removable liner 730 proximate the adhesive layer. In some embodiments, the removable liner is optically transparent in the near infrared region. A suitable optically clear liner is a 2 mil PET CIS Coating F-36 available from MPI. Having an optically transparent removable liner may provide the benefit of enabling measurements, calibrations, sensor checking, and other steps to be carried out prior to removing the liner and adhering the patient interface to the patient.

Figure 8:
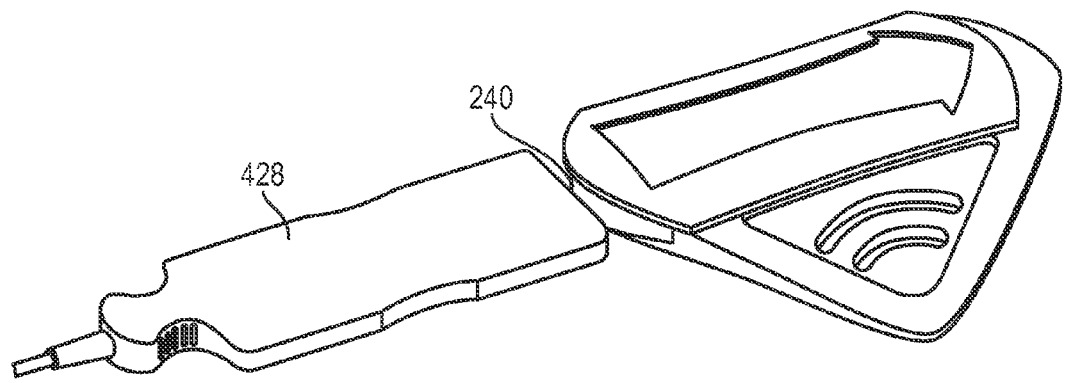
FIGS. 8-10 are schematic perspective views of a sensor being inserted into a pocket of a patient interface, in accordance with an embodiment of the invention.
Figure 9:
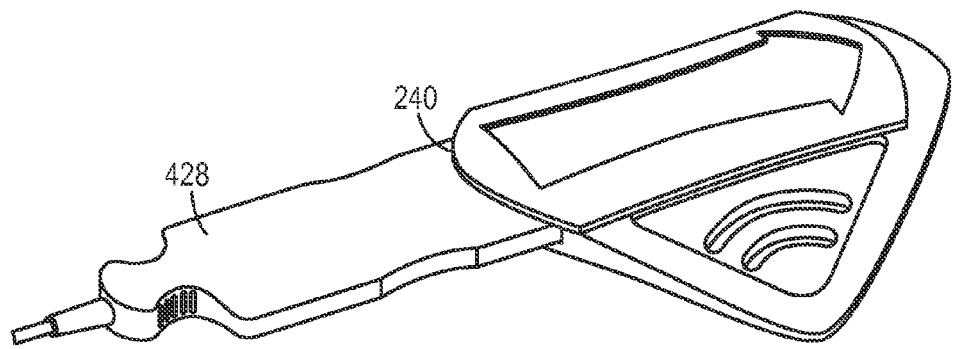
Figure 10:
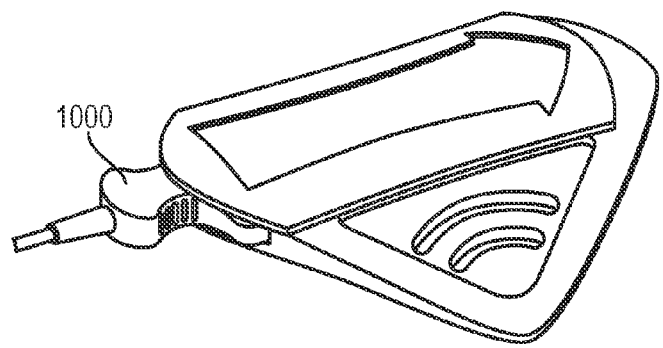

Referring to FIGS. 8 and 9, in use, an optical sensor 428 may be slid into the pocket 240 of the compliant element. An arrow 800 may be defined on the rigid component 245, indicating the direction in which the optical sensor should be inserted, thereby facilitating placement of the optical sensor. Referring to FIG. 10, when the optical sensor is fully inserted into the pocket, a tail end 1000 of the sensor may extend outside the pocket. This configuration allows the sensor to be easily grasped and removed from the compliant element.

Figure 11A:
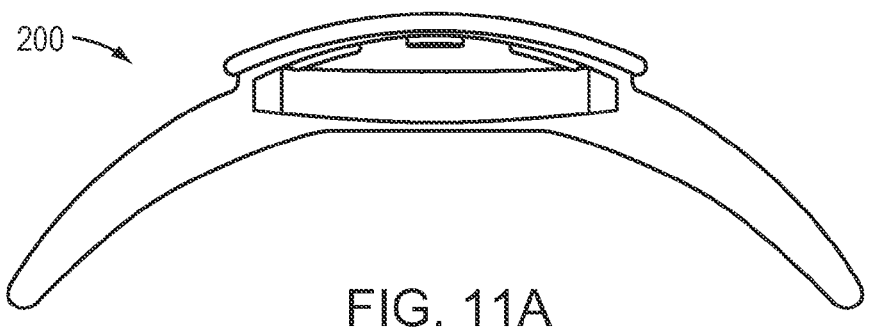
FIGS. 11a-11c are schematic solid model views of a patient interface in accordance with an embodiment of the invention.
Figure 11B:
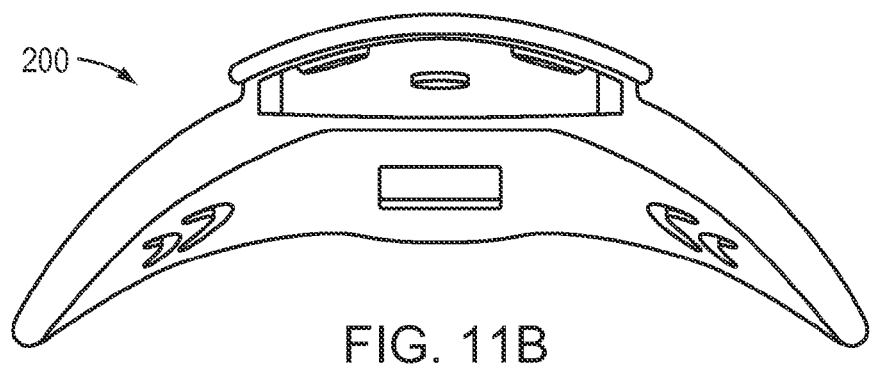
Figure 11C:
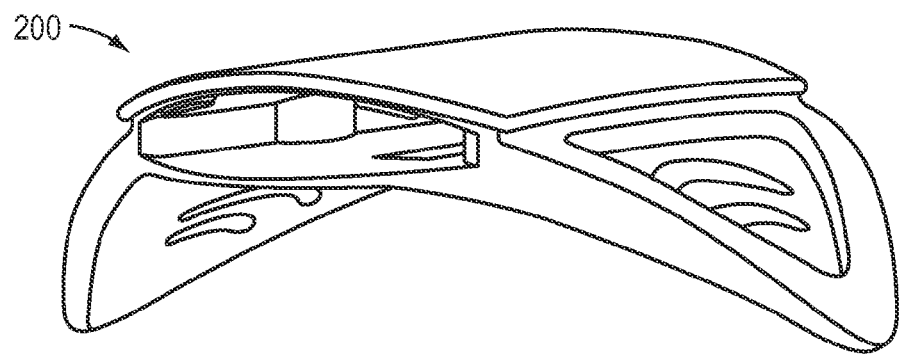

FIGS. 11a-11c provide alternative views of the patient interface 200, without an inserted optical sensor.

Figure 12:
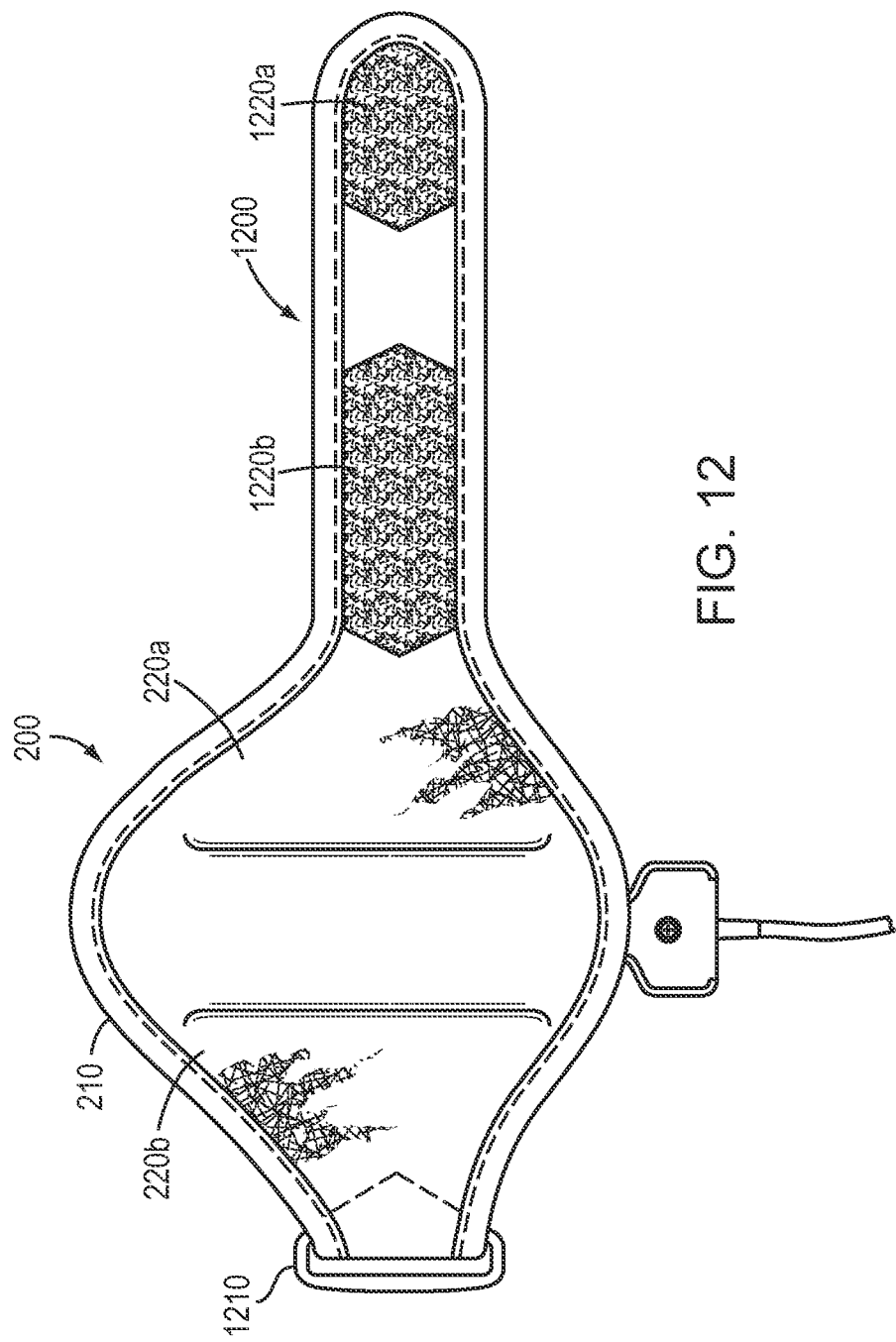
FIGS. 12-15 are schematic views of a patient interface, in accordance with an alternative embodiment of the invention.
Figure 13:
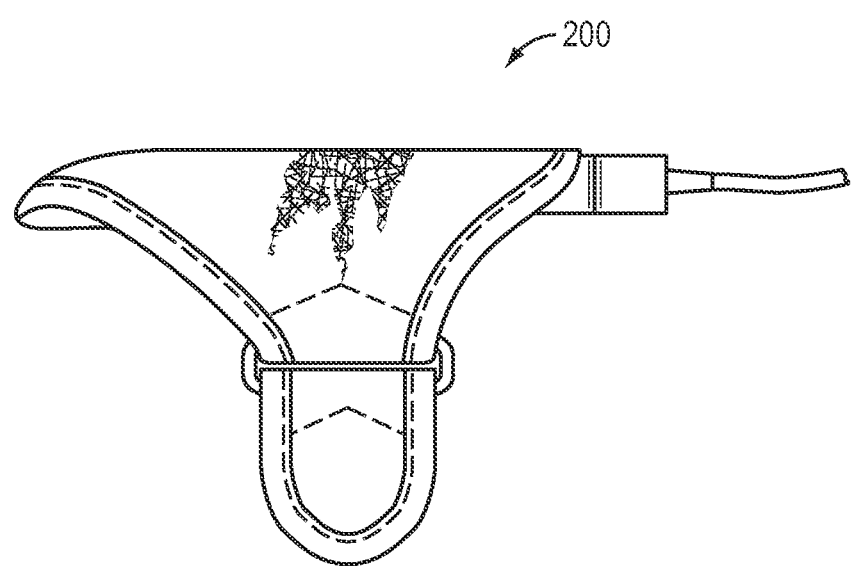

Referring to FIG. 12, in some embodiments, the patient interface 200 may include a compliant element 210 made from a flexible material, such as fabric. A strap 1200 may be attached to the first wing 220a of the compliant element, and a fastener 1210, e.g., a buckle, may be attached to the second wing 220b of the compliant element. Referring also to FIG. 13, the fastener may be configured to receive and secure the strap. The compliant element and the strap may be made from a continuous piece or pieces of the same fabric layers.

In some embodiments, the strap may be attached to—or extend from—the two wings of the compliant element, such that the patient interface may be slipped over a body portion and secured, without the use of fasteners. In such embodiments, a range of circumferences may be provided to allow secure placement of the optical sensor on different-sized patients.

Preferably, the fabric is waterproof so that it may protect, during use, an optical sensor disposed in the compliant element. In some embodiments, the fabric is breathable thereby increasing the patient's comfort. A suitable fabric may be a polyurethane laminated stretch knit polyester fabric, such as a 1 mil thick AKASOFT PUL polyester knit fabric having a thickness of 1 mil, available from AK Associates Laminated Solutions, based in Jackson, N.J. In some preferred embodiments, the fabric may be stretchable to assist in the firm placement of the optical sensor. For example, it may have a two-way stretch, e.g., stretching along a length of the strap. In some embodiments, the fabric may have a four-way stretch. The fabric may be stretchable up to 200%, e.g., 160% along the length of the strap. If a fabric is excessively stretchable, it may be pulled too tight and occlude blood flow in the body part to which it is attached.

The fastener 1210 may be a buckle, such as an LP loop available from American Cord & Webbing, based in Woonsocket, R.I. Other types of fasteners may also be used, e.g., a sewable loop, a cam buckle, a single bar slide, a post and slot, snaps, etc.

To assist with making a snug closure, hook-and-loop fasteners 1220a, 1220b may be disposed on the strap 1200, e.g., VELCRO hoop-and-loop fasteners. The hook-and-loop fastener strips of e.g., 1.5"-2" in width may be used. The hook portion 1220a is preferably relatively short, e.g., 1.5"-2.25' in length, and the loop portion 1220b is preferably longer, e.g., 3.5"-40", depending on the application for which the compliant element will be used.

Figure 14:
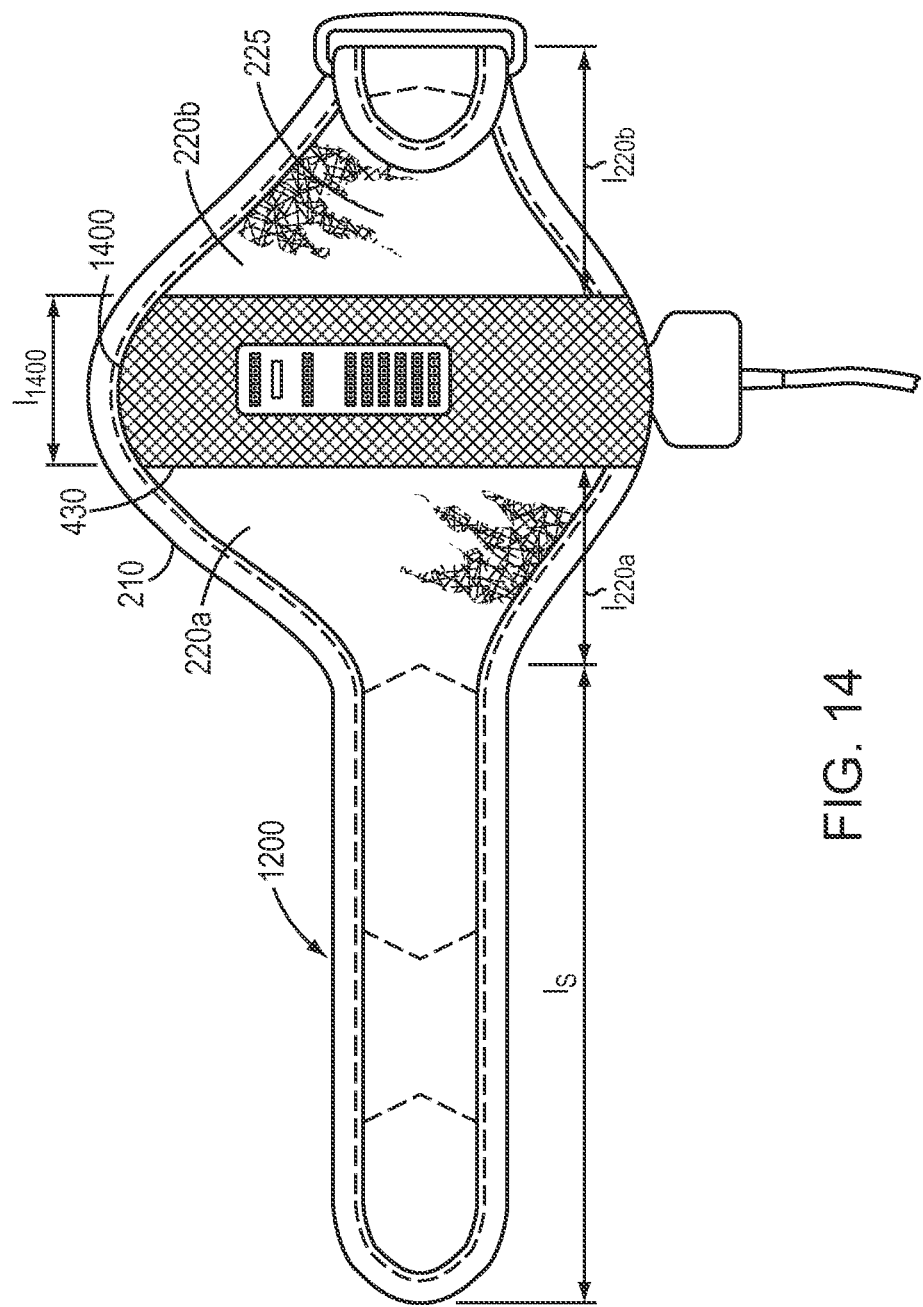
Figure 15:
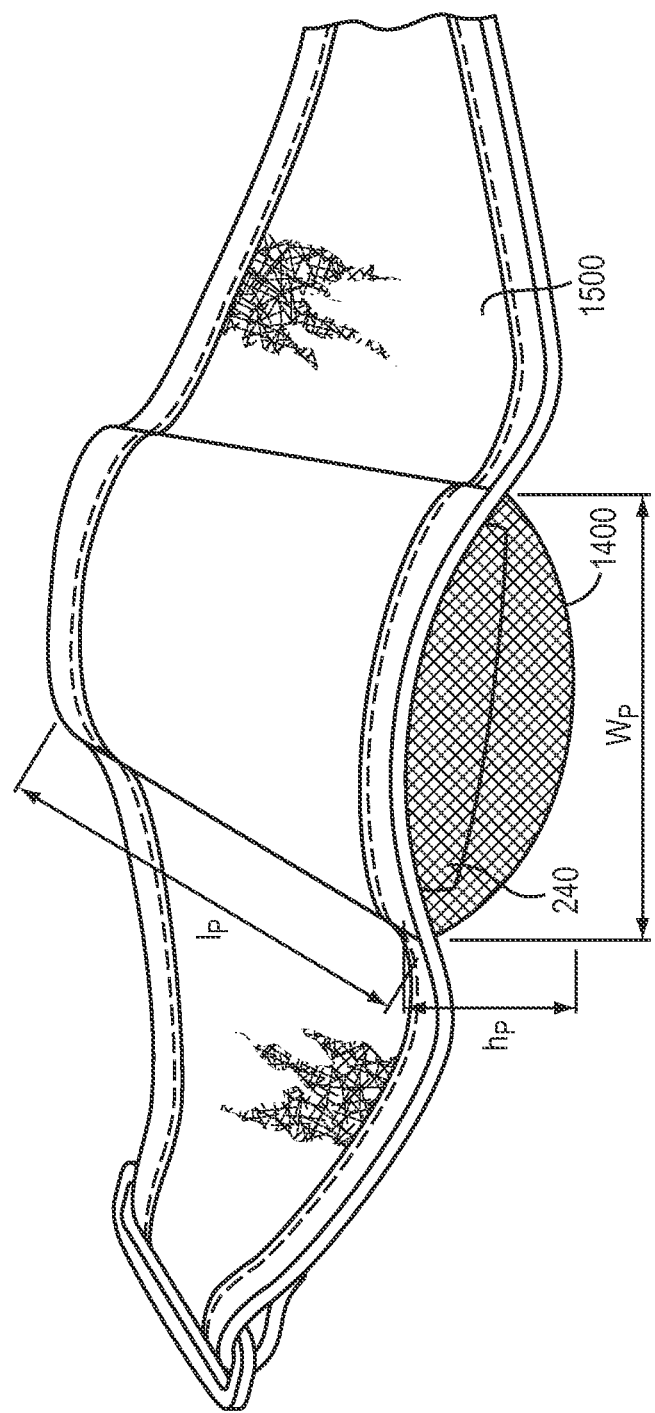

Referring to FIGS. 14 and 15, the contact surface 225 of the compliant member may include a central gripping portion 1400 having an opening 430 defined therethrough. The gripping portion 1400, in conjunction with the fabric compliant element, may define the pocket 240 for holding an optical sensor. Accordingly, the pocket has a lower wall defined by the gripping portion and an upper wall defined by fabric. As discussed above, the pocket may be sized and configured to receive the sensor with a sliding interference fit. For example, the pocket may have a width $w_p$ of about 1.875", a height $h_p$ of about 1", and a length $l_p$ of about 4.7".

The gripping portion 1400 may include a non-slip material that has a textured surface, e.g., nubs, waffle weave, random texture, etc. The non-slip material may provide a higher level of friction with skin than the fabric, to provide additional grip. Suitable materials include compliant rubber or polyurethane. Preferably, the gripping portion material is minimally elastic, to reduce the potential of the optical sensor shifting with respect to the opening 430. The strap 1200 may be configured, in conjunction with the compliant element, to encircle a portion of a patient's body. Accordingly, strap and compliant element together may have a length selected from a range of about 6" to about 60". For example, the strap may have a length $l_s$ of 7", a wing 220a proximate the strap may have a $l_{220a}$ of 2.25", the grip portion may have a width of 2", and the wing 220b distal from the strap may have a length $l_{220b}$ of 2.75".

A binding 1500 may be used to hold together a top layer of fabric, a bottom layer of fabric, and the gripping portion. Preferably, the material of the binding 1500 is similar to the fabric used for the top and bottom layers of the compliant element, e.g., similar in terms of stretchability and being waterproof.

Figure 16:
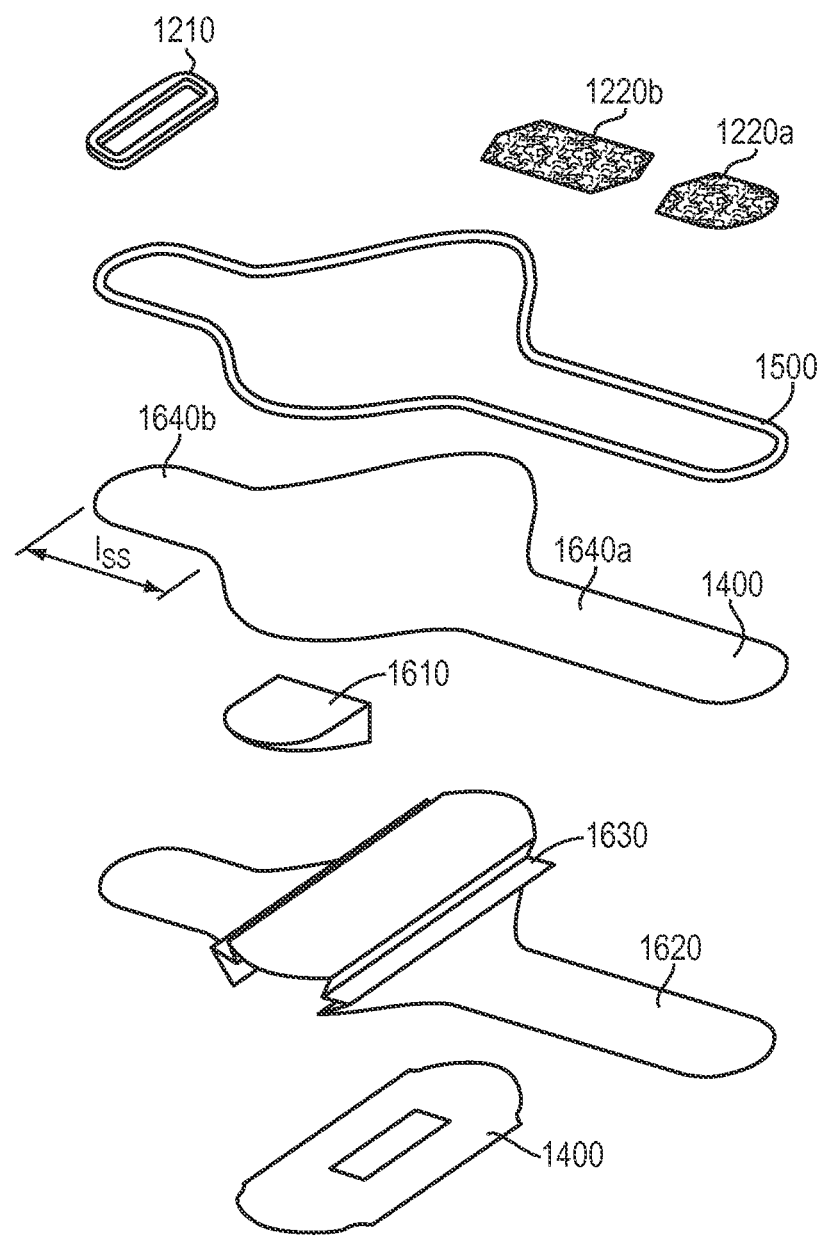
FIG. 16 is an exploded view of the patient interface of FIGS. 12-15.

Referring to FIG. 16, the components of a compliant element may include the following: a fastener 1210, hook-and-loop fasteners 1220a, 1220b, a binding 1500, a top fabric layer 1600, nose padding 1610, a bottom fabric layer 1620, and gripping portion 1400.

The top and bottom layers of fabric may be made from any of the types of fabrics discussed above.

Figure 17:
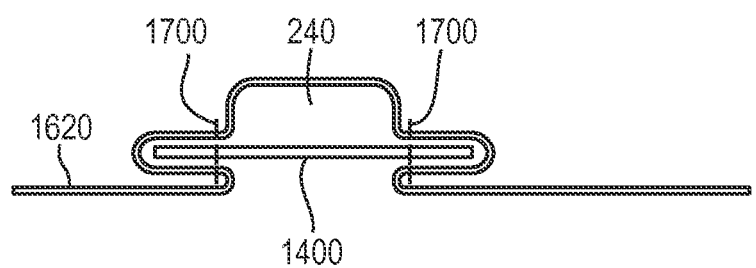
FIG. 17 is a schematic view of a gripping portion attached to a bottom layer of fabric, in accordance with an embodiment of the invention.

The top fabric layer may have the dimensions given above for the fabric compliant element. Referring also to FIG. 17, the bottom fabric layer 1620 may have a somewhat wider middle section, to allow folds 1630 to be made in the bottom fabric layer 1620. These folds allow sufficient room in the pocket to receive the optical sensor. An extra amount of fabric may be included in the bottom layer to provide enough room for the optical sensor and to fold the fabric over the edges of the gripping portion 1400. For example, an extra 1-5", preferably 1¾" of bottom layer fabric may be provided per edge of the gripping portion 1400. A seam 1700 may be sewn through the folded bottom layer fabric and the gripping portion on three sides of the gripping portion to create the pocket 240.

The fabric layers may define two straps: a first strap 1640a, e.g., a longer strap, to which hook and loop fasteners may be attached, and a second strap 1640b, e.g., a shorter strap, to which the fastening element may be attached. The shorter strap 1640b may have a length $l_{ss}$ that is sufficiently long to allow the attachment of a fastening element by looping the shorter strap 1640b through the fastening element, e.g., 1"-12", preferably 1⅝".

The nose padding may be a soft material such as polyester fiber batting, wool, cotton, foam, etc. It may be included at an end of the compliant element remote from an open end of the pocket. Without the nose padding, in view of the height of the optical sensor to be used with the compliant element, the nose of the compliant element may lift up away from the patient during use. The nose padding provides additional force in the nose to keep it down against the patient. The nose padding may have approximately the same width as the optical sensor, e.g., about 2". Preferred dimensions include a length of about 1", a height of about ⅝" at an end to be disposed near the optical sensor, with the height tapering down to about ⅛" inches at the tip of the nose. In an exemplary process, the components may be assembled as follows. As one of skill in the art will readily recognize, the order of the steps may be altered. In some embodiments, the fabric compliant member may be assembled by first sewing the hook-and-loop fasteners 1220a, 1220b to the longer strap 1640a defined by the top fabric layer. In some preferred embodiments, polyester thread may be used to sew together the components of the fabric compliant member. The gripping portion 1400 may be sewn to the bottom fabric layer 1620 with a seam 1700 extending along three edges of the gripping portion to define the pocket 240, as discussed with respect to FIG. 17. Then, the top layer 1600, nose padding 1610, and bottom layer 1620 may be layered in the order shown. Subsequently, the binding 1500 may be folded around the edges of the assembly and a seam formed around the edge. The fastening element 1210 may be attached to the short strap 1640b by the short strap through the fastening element, folding the short strap, and sewing a seam parallel to a side of the fastening element.

An optically clear window 720 may be used in conjunction with the fabric compliant element, as described above.

A method of monitoring a condition of a patient may include inserting an optical sensor into a patient interface, and applying the patient interface to the patient. A measurement may be obtained with the optical sensor of a parameter related to the condition of the patient. Then, the patient interface may be removed from the patient, and the sensor may be removed from the patient interface. In some embodiments, the patient interface may be disposed of, and the optical sensor may be reused in a new patient interface to obtain an additional measurement.

In some situations, a sensor check of the optical sensor may be needed or preferred. In such cases, before applying the patient interface to the patient and prior to obtaining the measurement with the optical sensor, a sensor check of the optical sensor may be performed. Thereafter, the patient interface, containing the sensor, may be adhered to the patient. The sensor check may be performed while a transparent liner is disposed on the contact surface of the patient interface. After the sensor check is performed, the transparent liner may be removed, and the adhesive on the contact surface adhered to the patient.

While there may have been described certain embodiments, it should be understood that the various features and functions of the invention may be used in various combinations and permutations. Sizes, materials, and the like are described by way of example only and are not to be considered limiting. The invention is to be defined by the meaning of the attached claims, including all equivalents.

What is claimed is:

1. A patient interface for a reusable optical sensor, the patient interface comprising:
    a compliant element defining a pocket having an upper wall and a lower wall and configured to removably receive the reusable optical sensor, the lower wall of the pocket defining an opening therethrough, the compliant element including a first wing and a second wing configured for conformal placement on a patient's body; and
    a rigid guide component disposed along at least a portion of an outer surface of the upper wall of the compliant element for guiding the reusable optical sensor into the pocket;
    wherein the compliant element comprises a contact surface and the opening extends from inside the pocket through the lower wall to the contact surface.

2. The patient interface of claim 1, wherein the compliant element comprises a material selected from the group consisting of open celled foam, closed cell foam, natural rubber, synthetic rubber, and thermoplastic elastomer.

3. The patient interface of claim 2, wherein the compliant element comprises a moisture impervious surface.

4. The patient interface of claim 1, wherein at least one of the wings defines a ventilation opening therethrough, providing ventilation to the patient's skin when in use.

5. The patient interface of claim 1, wherein the compliant element is molded to define a curved shape and is sized and configured to conform to a portion of a patient's body selected from the group consisting of a deltoid, an upper arm, a calf, a thigh, a forearm, an upper back, and a lower back.

6. The patient interface of claim 1, wherein the compliant element comprises a nose disposed at an end of the compliant element remote from an open end of the pocket.

7. The patient interface of claim 6, wherein the nose is angled toward the contact surface.

8. The patient interface of claim 6, wherein the nose has a tapered profile.

9. The patient interface of claim 1, further comprising at least one upper wall protrusion to bias an optical sensor disposed in the pocket toward the lower wall of the pocket.

10. The patient interface of claim 1, further comprising at least one lower wall protrusion proximate an entrance of the pocket to facilitate retention of the optical sensor in the pocket.

11. The patient interface of claim 1, further comprising an adhesive layer disposed on at least a portion of the contact surface of the compliant element.

12. The patient interface of claim 11, wherein the adhesive layer comprises a transfer adhesive.

13. The patient interface of claim 11, further comprising a removable liner proximate the adhesive layer.

14. The patient interface of claim 13, wherein the removable liner is optically transparent.

15. The patient interface of claim 1, further comprising an optically clear window layer aligned with the lower wall opening.

16. The patient interface of claim 15, wherein the optically clear window layer further comprises an adhesive surface along at least a portion thereof.

17. The patient interface of claim 15, wherein the optically clear window layer comprises an optical tape.

18. The patient interface of claim 1 wherein the pocket is sized to receive the sensor with a sliding interference fit.

19. The patient interface of claim 1, wherein the rigid component comprises a material selected from the group consisting of a plastic, a metal, and a composite material.

20. The patient interface of claim 1, wherein the compliant element comprises fabric.

21. The patient interface of claim 20, further comprising a first strap attached to one of the two wings, the first strap being configured for encircling a portion of a patient's body.

22. The patient interface of claim 21, further comprising a fastener attached to another of the two wings, adapted to receive and secure the first strap.

23. The patient interface of claim 22, wherein a second strap is attached to the other of the two wings and the fastener is attached the second strap.

24. The patient interface of claim 21, wherein the first strap comprises a hook-and-loop fastener.

25. The patient interface of claim 20, wherein the lower wall of the pocket comprises a nonslip material.

26. A method of monitoring a condition of a patient, the method comprising the steps of:
    in a patient interface, the patient interface comprising:
        a compliant element defining a pocket having an upper wall and a lower wall and configured to removably receive the reusable optical sensor, the lower wall of the pocket defining an opening therethrough, the compliant element including a first wing and a second wing configured for conformal placement on a patient's body; and
        a rigid guide component disposed along at least a portion of an outer surface of the upper wall of the compliant element for guiding the reusable optical sensor into the pocket;

wherein the compliant element comprises a contact surface and the opening extends from inside the pocket through the lower wall to the contact surface;
inserting an optical sensor into the patient interface;
performing a sensor check of the optical sensor while a transparent liner is in place on an adhesive layer;
removing the transparent liner from the adhesive layer;
applying the patient interface to the patient, wherein the optical sensor is held directly against the adhesive layer;
obtaining a measurement with the optical sensor related to the condition of the patient;
removing the patient interface from the patient; and
removing the sensor from the patient interface.

27. The method of claim 26, further comprising disposing of the patient interface and reusing the optical sensor in a new patient interface to obtain an additional measurement.

* * * * *